United States Patent [19]

Reiser et al.

[11] Patent Number: 5,497,100
[45] Date of Patent: Mar. 5, 1996

[54] SURFACE CONDITION SENSING SYSTEM

[75] Inventors: Kurt Reiser, Agoura; Scott Y. Harmon, Oak Park; Jennifer M. Butler, Pacific Palisades, all of Calif.

[73] Assignee: Hughes Aircraft Company, Los Angeles, Calif.

[21] Appl. No.: 324,436

[22] Filed: Oct. 17, 1994

[51] Int. Cl.⁶ .................................................. G01N 22/04
[52] U.S. Cl. ........................... 324/643; 324/642; 324/647
[58] Field of Search ..................................... 324/637, 638, 324/639, 640, 642, 643, 647

[56] References Cited

U.S. PATENT DOCUMENTS

| | | | |
|---|---|---|---|
| 3,594,775 | 7/1971 | Fox | 340/234 |
| 3,596,264 | 7/1971 | Ciemochowski | 340/234 |
| 3,613,063 | 10/1971 | Ciemochowski | 340/234 |
| 3,634,753 | 1/1972 | Unterberger | 324/6 |
| 3,836,846 | 9/1974 | Overall et al. | 324/58.5 |
| 3,838,281 | 9/1974 | Dean et al. | 250/308 |
| 3,873,927 | 3/1975 | Overall | 328/4 |
| 3,882,381 | 5/1975 | Gregory | 324/61 R |
| 3,891,979 | 6/1975 | Braun et al. | 340/234 |
| 3,940,622 | 2/1976 | Stallabrass et al. | 250/338 |
| 3,976,270 | 8/1976 | Catchpole | 244/134 |
| 4,051,466 | 9/1977 | Protze | 340/234 |
| 4,054,255 | 10/1977 | Magenheim | 244/134 F |
| 4,327,286 | 4/1982 | Thoma | 250/231 |
| 4,333,004 | 6/1982 | Forgue et al. | 219/497 |
| 4,335,613 | 6/1982 | Luukkala | 73/599 |
| 4,379,227 | 4/1983 | Kovacs | 250/231 |
| 4,461,178 | 7/1984 | Chamuel | 73/599 |
| 4,470,123 | 9/1984 | Magenheim et al. | 324/640 X |
| 4,570,881 | 2/1986 | Lustenberger | 244/134 |
| 4,604,612 | 8/1986 | Watkins et al. | 340/582 |
| 4,649,713 | 3/1987 | Bezek | 62/140 |
| 4,745,803 | 5/1988 | Haavasoja | 73/170 |
| 4,766,369 | 8/1988 | Weinstein | 324/61 R |
| 4,775,118 | 10/1988 | Daniels | 244/134 |
| 4,797,660 | 1/1989 | Rein, Jr. | 340/583 |
| 4,805,070 | 2/1989 | Koontz et al. | 361/286 |
| 4,808,824 | 2/1989 | Sinnar | 250/339 |
| 4,831,493 | 5/1989 | Wilson et al. | 361/286 |
| 4,851,817 | 7/1989 | Brossia et al. | 340/583 |
| 4,873,510 | 10/1989 | Khurgin | 340/580 |
| 4,882,574 | 11/1989 | Khurgin | 340/581 |
| 4,936,060 | 6/1990 | Gelinas et al. | 52/1 |
| 4,980,673 | 12/1990 | Kleven | 340/581 |
| 4,996,493 | 2/1991 | Monat et al. | 324/699 |
| 5,005,005 | 4/1991 | Brossia et al. | 340/604 |
| 5,040,411 | 8/1991 | Medzius | 73/73 |
| 5,095,754 | 3/1992 | Hsu et al. | 73/602 |
| 5,134,380 | 7/1992 | Jonas | 324/674 |
| 5,180,122 | 1/1993 | Christian et al. | 244/134 |
| 5,188,426 | 2/1993 | Stolarczyk et al. | 299/1.2 |
| 5,191,791 | 3/1993 | Gerardi et al. | 73/178 R |
| 5,384,543 | 1/1995 | Bible et al. | 324/644 |

OTHER PUBLICATIONS

"Contactless determination of the properties of water films on roads", Hertl et al., Journal of Physics and Scientific Instruments, 21(10), Oct. 1988, pp. 955–958.

"Discrimination of Ice from Water in Clouds by Optical Remote Sensing", Pilewskie et al., Atmospheric Research, 21(1987), pp. 113–122.

"Microwave Ice Thickness Sensor", by Werner Koppl, Dept. Staff Scientist, Martin Marietta Corporation, Denver, Colorado, pp. 146–147. Wednesday, May 19, 1971 (0950–1230) ESL—The Engineering Societies Library, New York, NY.

*Primary Examiner*—Kenneth A. Wieder
*Assistant Examiner*—Glenn W. Brown
*Attorney, Agent, or Firm*—V. D. Duraiswamy; W. K. Denson-Low

[57] ABSTRACT

A surface condition sensing system includes a frequency controlled source of electromagnetic power adapted to produce a band of selected frequencies which are directed to a surface under examination. A monitoring circuit compares transmitted and reflected electromagnetic power as a function of frequency from the surface, and generates a plurality of absorption signals representing the difference between the amplitude of the transmitted signal with the corresponding amplitude of the reflected signal. An evaluator circuit generates a surface condition signal representing the results of a comparison between the plurality of absorption signals with known surface models. A control circuit generates a status signal representative of the surface condition. The system can be configured as a road condition sensor or as an aircraft ice detection sensor.

25 Claims, 4 Drawing Sheets

SURFACE CONDITION SENSING SYSTEM

BACKGROUND OF THE INVENTION

1. Field of the Invention

This invention relates in general to surface condition sensing systems, and, more particularly, to ice and water detection systems for roadways and ice detection systems for aerodynamic structures of aircraft.

2. Description of the Related Art

Ice and water build-up on surfaces can pose deadly problems for certain kinds of transport.

Wet or icy roads can be extremely hazardous for vehicle drivers. For instance, in 1981, authorities in the United Kingdom reported that approximately one third of all vehicle collisions took place on wet roads. Studies on traction indicate that the presence of ice can significantly reduce traction. Because current traction control algorithms are optimized for one surface situation only (for example, dry roads), current antilock braking systems (ABS) are only 50% efficient on ice compared to their operation on a dry roadway. If traction control and ABS systems could be informed about the presence of water or ice on the roadway, vehicle safety could be significantly improved. Also, fixed ice detection systems mounted above or within bridges or other ice-prone areas could alert approaching drivers as to the presence of hazardous ice or water.

Likewise, icing, or ice layer build-up on aircraft wings, is a major concern of pilots flying not only in the winter months, but also at high altitudes where the moisture and constant cold temperature can cause ice to form in an otherwise cloudless sky. Once ice layers form on aircraft wings, the ice layers disturb the laminar flow over the wing, resulting in a loss of lift and the creation of dangerous flying conditions. Many air crashes have been traced to undetected icing on the wings.

Previous road or aircraft wing condition sensing systems were generally static in nature and required the temperature of the road bed or visually observed wing surface in order to make a decision about the presence of ice. A thermocouple or other means had to be placed on or in the road or surface in order to provide the needed temperature information.

The present invention, in contradistinction, infers the presence of ice from microwave signatures alone, making the invention completely contactless and capable of being carried by a vehicle to perform real time sensing of the road condition on which the vehicle is moving, or to constantly monitor for ice build-up on an aircraft in flight or on the ground.

Also, previous devices using a single microwave frequency to find water depth on a road surface have been limited to monitoring thin layers of ice or have required the associated measurement of road temperature and atmospheric humidity to infer the presence of ice. Another one of the innovative aspects of the present invention is the reliable detection of ice or water layers on a surface through processing of reflectance as a function of a range of microwave frequencies without the need for concurrent measurement of the surface temperature.

OBJECTS AND SUMMARY OF THE INVENTION

Therefore, it is an object of the present invention to provide a surface condition sensor that is movable with a vehicle and can detect the road condition in real time.

It is another object of the present invention to provide a surface condition sensor that can be permanently affixed to a bridge, overpass or even mounted in the roadway.

It is still another object of the present invention to provide a wing surface sensing device that can detect icing or water build-up on an aircraft wing.

The present invention uses a range of microwave frequencies to detect the presence of water or ice on road or the like surfaces. Water, ice, asphalt and concrete have different reflection and absorption properties and characteristics for various wavelength radiations. The present invention uses simple signal processing techniques to distinguish possible different conditions of surfaces based on their differing microwave signatures.

The present invention then is able to detect both ice and water without contacting the surface to be examined. It also scans a range of frequencies for more reliable detection of the surface's condition.

The present invention has a number of applications in current vehicle systems such as providing surface condition information to antilock braking systems (ABS); traction control systems; four wheel steering; adaptive chassis; and driver warning systems.

The present invention offers the following advantages over existing systems: completely contactless sensing; no reliance on external means of temperature and humidity measurement; the ice depth can be accurately measured and the rate of ice accumulation or decrease can be measured.

The novel features of construction and operation of the invention will be more clearly apparent during the course of the following description, reference being had to the accompanying drawings wherein has been illustrated a preferred form of the device of the invention and wherein like characters of reference designate like parts throughout the drawings.

DESCRIPTION OF THE PREFERRED EMBODIMENT

A preferred form of the invention, as embodied in a road condition sensing system, is now described.

Figure 1:
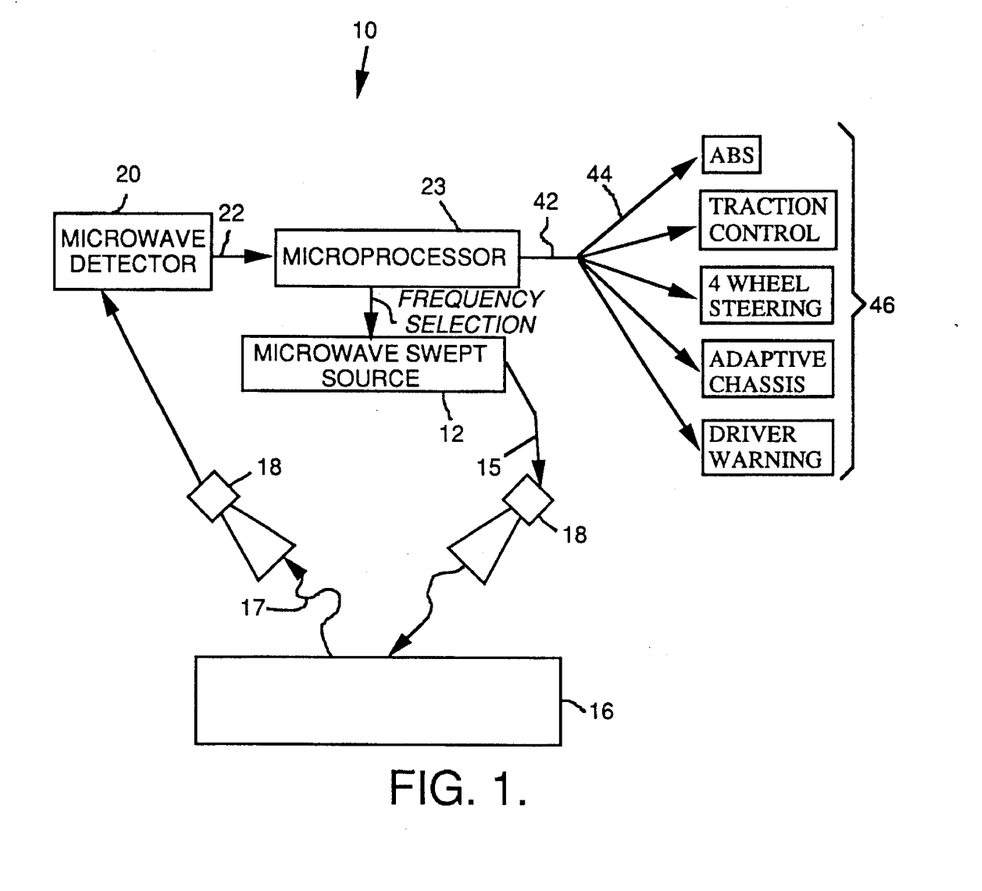
FIG. 1 shows a system block diagram of the present invention embodied in a road condition sensor.

The present invention as embodied in a system 10 for detecting wet, icy and dry conditions on a surface such as a roadway, is illustrated in FIG. 1. System 10 comprises a swept or stepped transmitter 12 adapted to produce energy in a band of frequencies preferably in the range of about 1 to about 90 GHz (which will hereinafter be referred to, for the sake of brevity, as 'microwave power' although it includes microwave and millimeter frequencies). Preferably the transmitter 12 is voltage controlled to produce microwave power over a band of frequencies in the range of about 1 to about 90 GHz.

A frequency control circuit (which can either be part of the transmitter 12 or a separate circuit) selectively controls the range of frequencies produced by the microwave transmitter 12. If the transmitter 12 is a voltage controlled transmitter whose frequency can be shifted by varying its input voltage, the sweep control circuit can be a varying voltage circuit or ramping circuit that has as an output a continuously varying range of voltages that are provided as an input to the voltage controlled swept or stepped microwave transmitter to cause the frequency output of the transmitter to vary likewise continuously within the band of frequencies.

Preferably the frequency control signal is periodic over a preselected time period so as to provide for consistency and accuracy in the system. In other alternate embodiments of the present invention, the transmitter may be varied using any known method, such as, but not limited to, being swept or stepped through the frequency band, as long as a synching signal provides the processing means a reference standard against which to process the reflected signals.

A radiating member, such as an antenna, coax or other element including a waveguide, such as found in a transmitting horn antenna 14 illustrated in the Figures, directs the broadband microwave power signal 15 to a surface 16 to be examined by the system 10.

While the present invention may be embodied in a system having a monostatic configuration where only a single antenna or horn is used for both transmission and reception of signals, it is preferred in many instances to use a second waveguide, such as a receiving horn antenna 18, to receive and direct microwave signals 17 reflected from surface 16 to a microwave detector circuit 20. Obviously other transmitting and receiving antenna arrays are also possible and included in the invention.

Microwave detector circuit 20 preferably includes an electromagnetic power detector, such as a microwave signal monitoring circuit for comparing microwave power as a function of frequency transmitted into and reflected from surface 16. Microwave detector circuit 20 generates a plurality of signals 22 indicating the power reflected from surface 16. Signals 22 can be processed to be representative of the difference between the amplitude of the microwave signals 15 transmitted into surface 16 and the corresponding amplitude of the microwave signals 17 reflected from surface 16 for each selected frequency in the range of microwave frequencies generated by transmitter 12. Alternatively, signals 22 can be compared to calibration signatures collected over wet, dry and icy conditions.

Figure 2A:
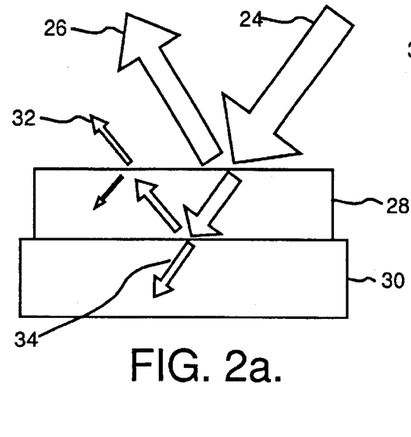
FIGS. 2a and 2b are cross-sectional views showing in idealized form reflection of microwave energy by water and ice layers on a road surface.
Figure 2B:
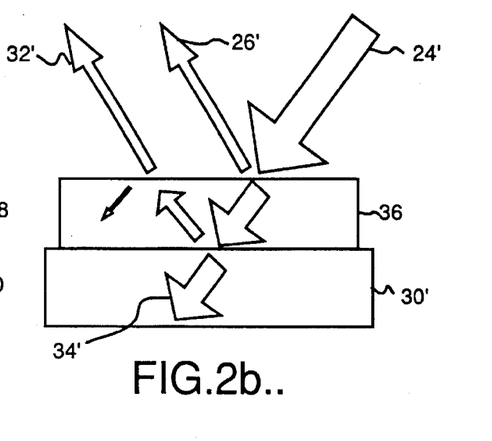

FIGS. 2a and 2b illustrate the reflection of microwave power by a water and an ice layer overlying a road surface respectively.

In FIG. 2a, a large portion of the incoming microwave energy 24 is reflected as energy 26 by the water surface 28 on road surface 30. A smaller amount of energy 32 can be reradiated from the road bed 30 and transmitted through the air-ice interface or air-water interface, with the remainder of the energy being absorbed and not reflected 34.

In FIG. 2b, a fraction 26' of the incoming microwave signal 24' is reflected by the ice layer 36 on road surface 30'. Since ice does not absorb microwave power as strongly as water, reflected power 26' and the reflected power 32' give rise to an interference pattern.

Figure 3:
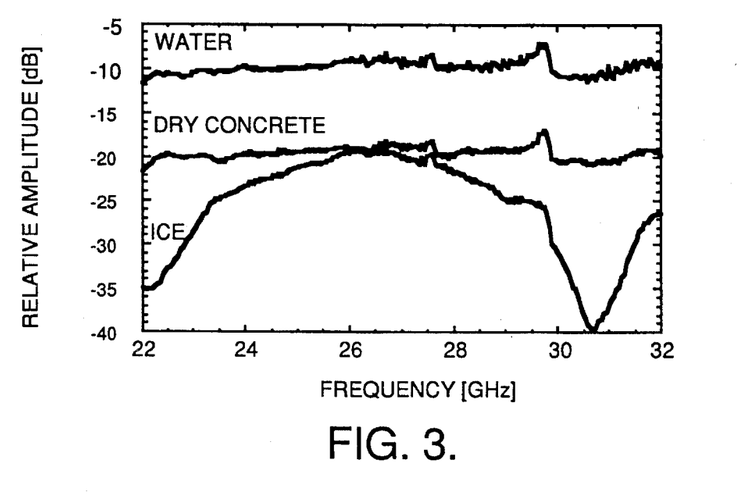
FIG. 3 is a graph of laboratory data showing the relative reflected amplitude of microwave power as a function of frequency from an observed surface irradiated from above by an RF source.

Each of these conditions of an ice or a water layer on a surface of known composition has a distinctive and identifiable signature as shown by the laboratory data appearing in the graphs in FIG. 3 showing the distinct differences between amplitude versus frequency signatures for wet, dry and icy road conditions on a concrete road.

System 10 is preferably controlled by a microprocessor 23 operating as described below.

Microprocessor 23 has stored in its memory a predetermined sequence of surface profile signals or surface models (hereinafter referred to as 'surface profiles') representing a surface covered with a layer of ice, a surface covered with a layer of water, and a dry surface determined from previous experimental testing of such conditions.

Microprocessor 23 acts as an evaluator, generating, for each plurality of signals 22, a surface condition signal 42 by quantizing and comparing the minimum return amplitude of microwave power sensed over the whole frequency band, with the sequence of surface profiles stored in its memory.

Microprocessor 23 may also act as an evaluator of the received signals, by being programmed to detect the shape of the returned signals, and the frequency location and spacing of detected interference minima, etc., without having surface profiles stored in its memory.

Microprocessor 23 also contains control circuitry for generating a status signal 44 in accordance with the surface condition signal 42 generated by the comparison between the plurality of signals 22 and the surface profiles stored in its memory. Microprocessor 23 can also generate a signal representing the detected ice depth and/or the change in depth over time.

Status signal 44 can be used as an input to vehicle warning or control systems 46 to display a warning light, sound an audio alarm or directly control braking, drive or traction systems of the vehicle.

Figure 4:
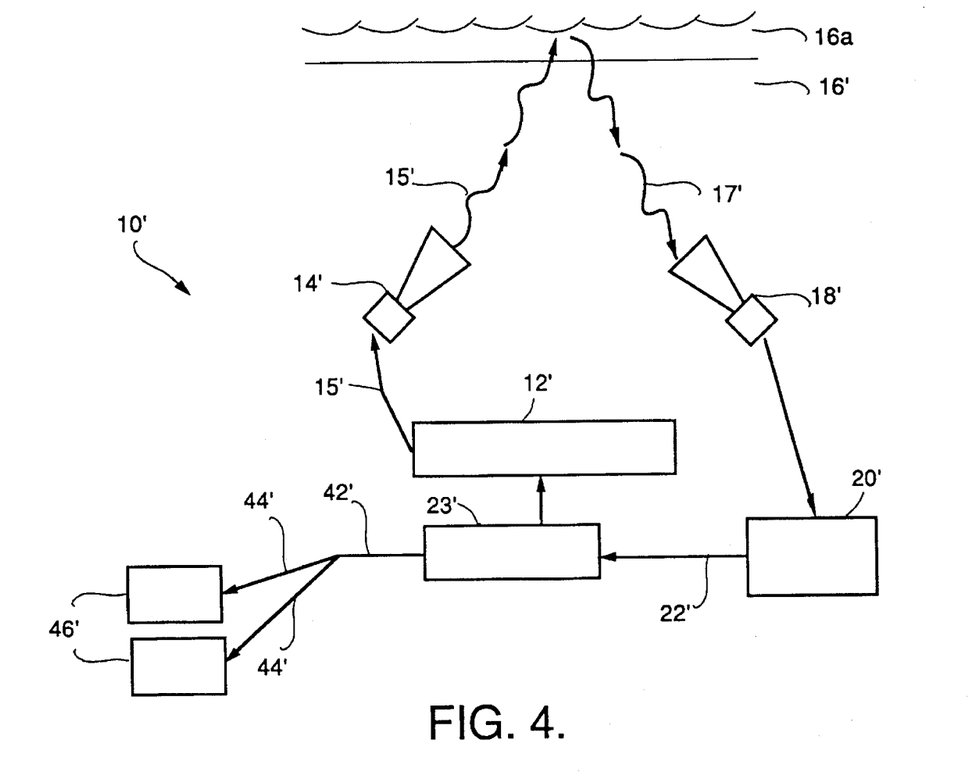
FIG. 4 shows a system block diagram of the present invention embodied as an embedded surface condition sensor and is a functional diagram of the system illustrated in FIG. 7 below.
Figure 5:
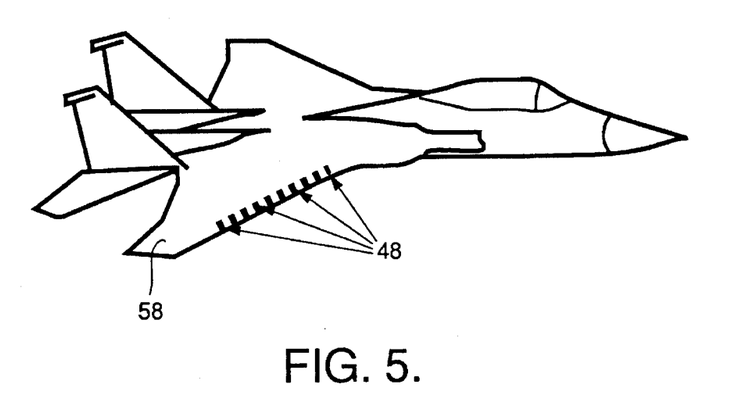
FIG. 5 is an illustration of how the embodiment of the invention illustrated in FIG. 4 can be embedded in an aircraft wing.
Figure 6A:
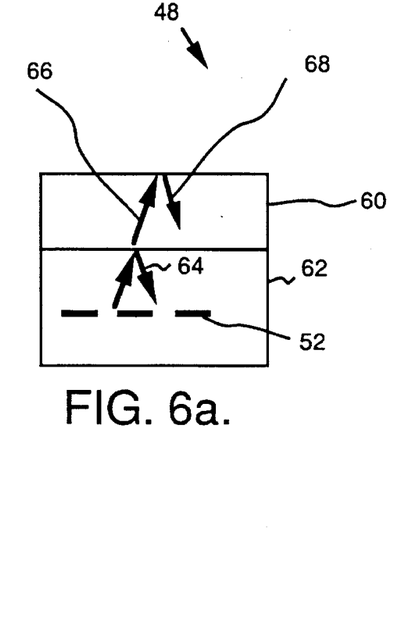
FIGS. 6a and 6b are cross-sectional views showing in idealized form reflection of microwave power by water and ice layers from the embodiment of the invention shown in FIG. 4.
Figure 6B:
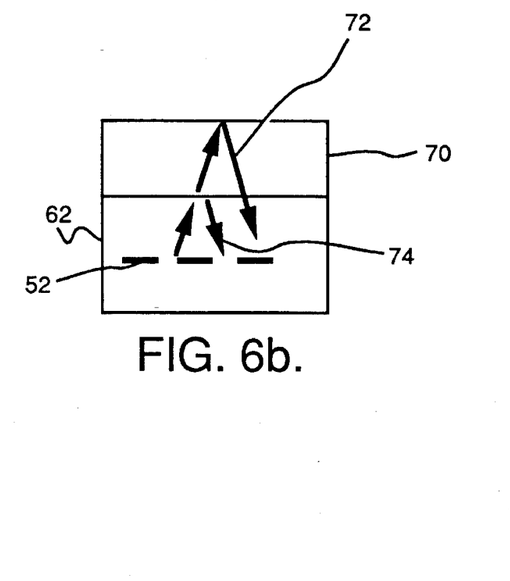

An alternate embodiment of the present invention is now described as an aircraft ice detection apparatus that is shown in FIGS. 4 through 6.

Generally, the structure described above for the road condition sensor also applies to the wing icing sensing system. Therefore, system components similar to previously discussed system components will be indicated in FIG. 4 by a similar numeral followed by a prime. To avoid repetition of aspects which are common to both embodiments and have already been discussed in connection with the road condition sensor embodiment, descriptive emphasis in the following description will be primarily placed on the unique aspects of this alternate embodiment.

The system 10' of this alternate embodiment comprises a swept or stepped microwave transmitter 12' adapted to produce microwave power over a band of microwave frequencies. Preferably transmitter 12' is systematically frequency varied, such as by voltage control, to produce microwave power with frequencies in a range of about 1 to about 90 GHz, or sub-bands within this frequency range, which can be optimally selected depending on the anticipated thickness of the layer most likely to be encountered.

A sweep control circuit (not illustrated) selectively controls the range of frequencies produced by the microwave transmitter 12'. If the transmitter 12' is a voltage controlled transmitter whose frequency can be shifted by varying its input voltage, the sweep control circuit can be a varying voltage circuit or ramping circuit that has as an output a continuously varying range of voltages that are provided as an input to the voltage controlled swept or stepped microwave transmitter to cause the frequency output of the transmitter to vary likewise continuously within the band of frequencies.

Likewise, it is within the scope of this invention to use a transmitter that is stepped or even frequency hopped through the selected frequency range.

Preferably the frequency control circuit may be periodic over a preselected time period, or may be asynchronous by providing the processor with an interrupt signal, or the processor may control the transmitter directly.

An antenna, such as a directional transmitting horn antenna 14', directs the band of microwave frequencies 15' to a surface 16' to be observed by the system 10'.

A second antenna, such as a receiving horn antenna 18', receives and directs microwave signals 17' reflected from surfaces 16' and 16a (an outer layer on top of surface 16') to a microwave detector circuit 20'. Obviously other transmitting and receiving antenna arrays such as stripline antennas, patch antennas and the like, and even a single monostatic transmitting/receiving antenna, are also possible and included in the invention.

Microwave detector circuit 20' preferably includes a signal monitoring circuit for comparing microwave power as a function of frequency transmitted into and reflected from surfaces 16' and 16a. Microwave detector circuit 20' generates a plurality of signals 22' indicating the power reflected from surfaces 16' and 16a. Signals 22' can be processed to be representative of the difference between the amplitude of the microwave signals 15' transmitted into surfaces 16' and 16a and the corresponding amplitude of the microwave signals 17' reflected from surfaces 16' and 16a for each selected frequency in the range of microwave frequencies generated by transmitter 12'. Alternatively, signals 22' can be compared to calibration signatures collected over wet, dry and icy conditions.

Since an aircraft ice sensing system must not alter the airflow over the aerodynamic structure itself, it is preferable that system 10' be embedded in the surface of the aerodynamic structure or encased in material generally transparent to microwaves and conformed to the surface.

Figure 7:
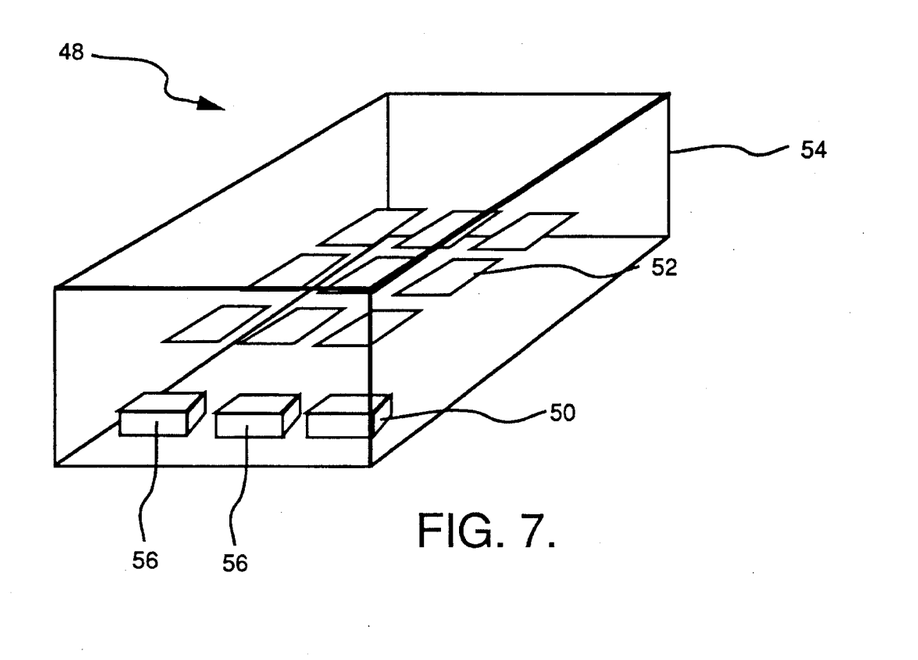
FIG. 7 is an illustration of how the embodiment of the invention illustrated in FIG. 4 can be embedded in a casing.

FIGS. 5 and 7 illustrate how an ice sensing system 10' can be embodied into a single encapsulated wing ice module 48 where a range of microwave frequencies is generated by a device such as a MMIC (Microwave Monolithic Integrated Circuit) chip 50 and transmitted by a patch antenna 52. Layers of ice or water forming on top of the casing 54 cause microwaves to be reflected back into the receiving antennas 52. One or more signal processing chips 56 are used to discriminate water from ice from a clean condition given the characteristic reflection signatures of each.

FIG. 5 illustrates a plurality of such wing ice modules 48 embedded in an aircraft wing 58. Each of the modules 48 is flush with the wing's surface so as not to modify the desired airflow over the airfoil, but since the casing 54 forms part of the airfoil itself and is transparent to the interrogating microwave signal, the system can still detect local accumulations of water or ice forming on the wing 58 and casing 54.

In order to reduce cost, weight and complexity in the system, a single RF source 50 can be used to generate the microwave energy for several ice detection modules 48.

FIGS. 6a and 6b are cross sectional views similar to those shown in FIGS. 2a and 2b described above. The major difference between these two pairs of Figures is that the surface of interest is flush with the outside of casing 54 and not directly exposed to the microwave radiation whereas the surface of interest is irradiated from above.

FIG. 6a shows a layer of water 60 covering the casing 62 forming a portion of the wing. Since water is very reflective and absorbent to microwave power, a microwave signal transmitted by the embedded antennae array 52 is reflected off the lower surface of the water layer 60 as energy 64. The microwave signal 66 entering the water layer 60 is absorbed as shown by arrow 68.

FIG. 6b shows a layer of ice 70 covering the casing 62 forming a portion of the wing. Since ice does not reflect microwave energy as well as water and does not absorb the signal, the power passes through as shown by arrow 72. This creates interference patterns caused by reflected signals 74 and 72 when a range of frequencies is swept or stepped through. Signal processing methods can then be used to distinguish an ice layer from a water layer by the known reflection and interference pattern characteristics of each.

Figure 8:
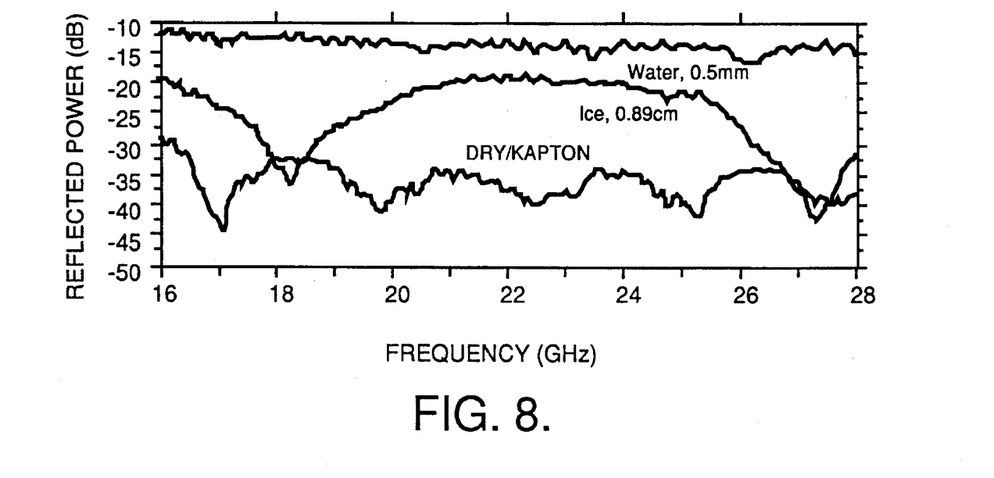
FIG. 8 is a graph of laboratory data showing the relative reflected amplitude of microwave power as a function of frequency from an observed surface which covers the radiating antenna.

Each of these conditions, namely ice or water layer on a surface of known composition has a distinct and identifiable signature as shown by the laboratory data presented in FIG. 8. This graph shows the distinct differences in amplitude versus frequency signatures of wet, dry and icy surface conditions of a kapton sheet covering a radiation horn antenna. The antenna system can itself be embedded into a casing that can itself form a portion of the monitored airfoil that is to be observed. The casing must of course be fabricated of a material such as plastic which enables transmission of microwave power.

One key advantage of this configuration is that the ice layer is sensed from the wing side outward, so that water or even deicing fluid on the wing cannot mask the true ice layer from the sensor as may occur in an inwardly directed radiating system or visual sensors where a layer of fluid may cover the ice layer and reflect signals falsely indicating the surface to be clean except for a fluid layer, the ice layer undetected and hiding underneath.

Another advantage of this configuration is that a change in the thickness of a detected layer can be determined by storing and processing sequential historical data, i.e., by noting a change in the reflected signals over an elapsed time period.

The signal monitoring circuit 20' can also be embedded in the casing for receiving and comparing microwave energy and frequencies transmitted to and reflected from the casing surface that is to be observed and can operate similar to that described above. The signal monitoring circuit 20' generates a plurality of reflection signals 22', each of which is representative of the difference between the amplitude of the microwave signal 15' transmitted to the observed surfaces 16' and 16a, and the corresponding amplitude of the microwave signal 17' reflected from the observed surfaces for a microwave frequency in the band of microwave frequencies. Alternatively, signals 22' can be compared to calibration signatures collected over wet, dry and icy conditions.

Once again, a microprocessor 23' preferably controls the overall system and has stored in its memory a predetermined sequence of surface profiles representing the reflection of microwave energy by a layer of ice and a layer of water.

Microprocessor 23' acts as an evaluator, generating, for each plurality of signals 22', a surface condition signal 42' by quantizing and comparing the minimum return amplitude of microwave power sensed over the whole frequency band, as represented by the plurality of signals 22', with the sequence of surface profiles stored in its memory, or by processing the reflected signals to determine frequency location or spacing or location of minima, etc.

Microprocessor 23' also contains control circuitry for generating a status signal 44' in accordance with the surface condition signal 42' generated by the comparison between the plurality of signals 22' and the surface profiles generated by signal processing steps described above and stored in its memory.

Status signal 44' can be used as an input to aircraft warning or control systems 46' to display a warning light, sound an audio alarm or directly control de-icing systems of the aircraft.

A general operational description of one preferred embodiment of the invention described above is now given.

Microwave emission and reception occurs as follows: The microprocessor outputs a range of voltages, either continuously or in a known pattern with a synchronizing signal, to the controllable frequency source, such as a swept or stepped microwave transmitter, causing the frequency source to output a band of selected frequencies. A radiating system, such as a small microwave horn, or other antenna, is mounted in association with the surface that is to be observed, i.e., for an automobile, beneath the automobile and in front of a tire, or over a bridge, overpass or roadway or even in the roadway itself or for an aircraft, embedded into an aerodynamic surface. It broadcasts the frequency band toward the observed surface. A receiving antenna, which may be the same radiating system as transmits the microwave signal and microwave power protector, supplies the microprocessor with measures of reflected power encoded as voltages.

Reflected signal signature processing in the invention occurs as follows: As can be seen in the laboratory data of FIG. 3, ice can be distinguished from other surface types through the detection of periodic interference minima received over the range of microwave frequencies. A simple technique which can differentiate ice from dry and dry from wet signatures gathered on real roads is to quantize the minimum return amplitude sensed over the whole frequency band. Since the frequency spacing of local minima in ice signatures is a function of ice depth, alternative methods would locate individual minima, calculate the spacing between minima and infer ice depth. If computed ice depths were impossibly large or small, the signature can be dismissed as noisy. Average amplitude can be used to determine the presence of water. In any case, signatures of the various surfaces are sufficiently different that simple and fast signal processing techniques can certainly be used to identify dry, wet and icy conditions.

The invention described above is, of course, susceptible to many variations, modifications and changes, all of which are within the skill of the art. It should be understood that all such variations, modifications and changes are within the spirit and scope of the invention and of the appended claims. Similarly, it will be understood that Applicant intends to cover and claim all changes, modifications and variations of the example of the preferred embodiment of the invention herein disclosed for the purpose of illustration which do not constitute departures from the spirit and scope of the present invention.

What is claimed is:

1. A surface condition sensing system comprising:

a source of electromagnetic power for producing signals in a band of frequencies;

sweep control means, operatively connected to said source, to control selectively the frequencies produced by said source in said frequency band periodically over a predetermined time interval by continuously outputting a control signal to said source to cause the frequency output of said source to vary continuously within said band of frequencies;

means for coupling said band of frequencies to a surface to be examined;

signal monitoring means for comparing power and frequencies transmitted into and reflected from said surface to be examined, and for generating a plurality of absorption signals, each of said absorption signals representative of the difference between the amplitude of the electromagnetic power transmitted into said surface and the corresponding amplitude of the signal reflected from said surface for a frequency in said band of frequencies;

evaluator means, connected to said signal monitoring means, for generating a surface condition signal, for each plurality of absorption signals, by quantizing and comparing the minimum return amplitude of power sensed over the whole frequency band, as represented by said plurality of absorption signals, with a sequence of surface profiles;

control means connected to said evaluator means for generating a status signal in accordance with said surface condition signal.

2. A surface condition sensing system, comprising:

a frequency sweepable source of electromagnetic power adapted to produce a band of known frequencies;

sweep control means operatively connected to said source to control selectively the frequencies produced by said source in said frequency band;

means for coupling said band of frequencies to a surface to be examined;

signal monitoring means for comparing electromagnetic power as a function of frequency transmitted into and reflected from said surface to be examined, and for generating a plurality of absorption signals, each of said absorption signals representative of the difference between the amplitude of the signal transmitted into said surface and the corresponding amplitude of the signal reflected from said surface for a frequency in said band of frequencies;

storage means having a predetermined sequence of surface profiles therein representing a surface covered with a layer of ice, a surface covered with a layer of water and a dry surface;

evaluator means, connected to said signal monitoring means and to said storage means, for generating for each plurality of absorption signals, a surface condition signal representing the results of a comparison between said plurality of absorption signals and said surface profiles;

control means connected to said evaluator means for generating a status signal in accordance with said surface condition signal.

3. A system as in claim 2 wherein said frequency sweepable source is a voltage controlled swept transmitter.

4. A system as in claim 3 wherein said sweep control means continuously outputs a range of voltages to said voltage controlled swept transmitter to cause the frequency output of said voltage controlled swept transmitter to vary continuously within said band of frequencies.

5. A system as in claim 4 wherein said output range of voltages of said sweep control means is periodic over a predetermined time interval.

6. A system as in claim 2 wherein said means for coupling said band of frequencies is an antenna.

7. A system as in claim 6 wherein said antenna is a horn antenna.

8. A system as in claim 2 wherein said signal monitoring means includes an antenna.

9. A system as in claim 2 wherein said evaluator means generates said surface condition signal by quantizing and comparing the minimum return amplitude of power sensed over the whole frequency band, as represented by said plurality of absorption signals, with said sequence of surface profiles.

10. An aircraft ice detection apparatus comprising:

a frequency controllable source of electromagnetic power adapted to produce a band of selected frequencies;

frequency control means operatively connected to said source to control selectively the frequencies produced by said source in said selected frequency band;

means for coupling said band of frequencies into a casing for reflection by a casing surface to be examined, said casing fabricated of a material which enables transmission of electromagnetic power;

signal monitoring means for comparing electromagnetic power as a function of frequency transmitted into said surface and reflected from said surface, and for generating a plurality of reflection signals, each of said reflection signals representative of the difference between the amplitude of the signal transmitted into said surface and the corresponding amplitude of the signal reflected from said surface for a frequency in said band of frequencies;

storage means having a predetermined sequence of surface profiles therein representing the reflection of electromagnetic power by a layer of ice and a layer of water;

evaluator means, connected to said signal monitoring means and to said storage means, for generating for each plurality of reflection signals, a surface condition signal representing the results of a comparison between said plurality of reflection signals and said surface profiles; and control means connected to said evaluator means for generating a status signal in accordance with said surface condition signal.

11. An aircraft ice detection apparatus as in claim 10 wherein said frequency controllable source is a voltage controlled swept transmitter.

12. An aircraft ice detection apparatus as in claim 11 wherein said frequency control means continuously outputs a range of voltages to said voltage controlled swept transmitter to cause the frequency output of said voltage controlled swept transmitter to vary continuously within said band of frequencies.

13. An aircraft ice detection apparatus as in claim 12 wherein said output range of voltages of said sweep control means is periodic over a predetermined time interval.

14. An aircraft ice detection apparatus as in claim 10 wherein said means for coupling said band of frequencies is an antenna.

15. An aircraft ice detection apparatus as in claim 14 wherein said antenna is a horn antenna.

16. An aircraft ice detection apparatus as in claim 10 wherein said signal monitoring means includes an antenna.

17. An aircraft ice detection apparatus as in claim 10 wherein said evaluator means generates said surface condition signal by quantizing and comparing the minimum return amplitude of electromagnetic power sensed over the whole frequency band, as represented by said plurality of reflection signals, with said sequence of surface profiles.

18. An aircraft ice detection apparatus as in claim 10 wherein said casing is fabricated of a plastic material.

19. An aircraft ice detection apparatus comprising:

a voltage controlled transmitter adapted to produce electromagnetic power in a band of selected frequencies;

frequency control means operatively connected to said transmitter to control selectively the frequencies produced by said transmitter in said frequency band periodically over a predetermined time interval by continuously outputting a range of voltages to said voltage controlled transmitter to cause the frequency output of said voltage controlled transmitter to vary continuously within said band of frequencies;

means for coupling said band of frequencies into a casing for reflection by a casing surface to be examined, said casing fabricated of a material which enables transmission of electromagnetic power;

signal monitoring means for comparing electromagnetic power as a function of frequency transmitted into said casing and reflected from said casing surface, and for generating a plurality of reflection signals, each of said reflection signals representative of the difference between the amplitude of the signal transmitted into said casing and the corresponding amplitude of the signal reflected from said casing surface for a selected frequency in said band of frequencies;

storage means having a predetermined sequence of surface profiles therein representing the reflection of electromagnetic power by at least one layer of ice and/or at least one layer of water;

evaluator means, connected to said signal monitoring means and to said storage means, for generating for each plurality of reflection signals, a surface condition signal representing the results of a comparison between said plurality of reflection signals and said surface profiles, and control means connected to said evaluator means for generating a status signal in accordance with said surface condition signal.

20. A surface condition sensing system, comprising:

a frequency variable source of electromagnetic power adapted to produce a selected band of frequencies;

frequency control means operatively connected to said source of electromagnetic power, to control selectively the frequencies produced by said source in said selected band of frequencies;

means for coupling said band of frequencies to a surface to be examined;

signal monitoring means for comparing electromagnetic power as a function of frequency transmitted into and reflected from said surface to be examined, and for generating a plurality of absorption signals, each of said absorption signals representative of the difference between the amplitude of the signal transmitted into said surface and the corresponding amplitude of the signal reflected from said surface for a selected known frequency in said band of frequencies;

storage means having a predetermined sequence of surface profiles therein representing at least one surface covered with at least one layer of ice, at least one surface covered with at least one layer of water, and at least one dry surface;

evaluator means, connected to said signal monitoring means and to said storage means, for generating for each plurality of absorption signals, a surface condition signal representing the results of a comparison between said plurality of absorption signals and said surface profiles;

control means connected to said evaluator means for generating a status signal in accordance with said surface condition signal.

21. A system as in claim 20 wherein said frequency control means causes the frequency output of said source to vary periodically over a predetermined time interval within said band of frequencies, and said frequency control means further generating a synchronizing signal representative of the periodicity of said frequency control means.

22. A system as in claim 21 wherein said evaluator means receives as input said synchronizing signal and generates said surface condition signal by quantizing and comparing the minimum return amplitude of microwave energy sensed over the whole frequency band, as represented by said plurality of absorption signals, with said sequence of surface profiles for each period of said frequency control means.

23. A system as in claim 21 wherein said evaluator means receives as input said synchronizing signal and generates said surface condition signal by quantizing and comparing the frequency location or the spacing between the minima in the return amplitude of microwave power sensed over the whole frequency band, as represented by said plurality of absorption signals, with said sequence of surface profiles for each period of said frequency control means.

24. A system as in claim 21 wherein said evaluator means receives as input said synchronizing signal and generates said surface condition signal by quantizing and comparing the frequencies at which the minimum return amplitude of microwave power sensed over the whole frequency band occurs, as represented by said plurality of absorption signals, with said sequence of surface profiles for each period of said frequency control means.

25. A surface condition sensing system, comprising:

a voltage controlled microwave source producing microwave power in a band of microwave frequencies;

sweep control means operatively connected to said source to control selectively the frequencies produced by said source in said microwave frequency band periodically over a predetermined time interval by continuously outputting a range of voltages to said source to cause the frequency output of said source to vary continuously within said band of frequencies;

means for coupling said band of microwave frequencies to a surface to be examined;

signal monitoring means for comparing microwave power as a function of frequency transmitted into and reflected from said surface, and for generating a plurality of absorption signals, each of said absorption signals representative of the difference between the amplitude of the microwave signal transmitted into said surface and the corresponding amplitude of the microwave signal reflected from said surface for a microwave frequency in said band of microwave frequencies;

storage means having a predetermined sequence of surface profiles therein representing a surface covered with a layer of ice, a surface covered with a layer of water, and a dry surface;

evaluator means, connected to said signal monitoring means and to said storage means, for generating for each plurality of absorption signals, a surface condition signal by quantizing and comparing the minimum return amplitude of microwave power sensed over the whole frequency band, as represented by said plurality of absorption signals, with said sequence of surface profiles;

control means connected to said evaluator means for generating a status signal in accordance with said surface condition signal.

* * * * *